(12) United States Patent
Fulton, Jr.

(10) Patent No.: US 6,169,110 B1
(45) Date of Patent: Jan. 2, 2001

(54) REJUVENATING THE SKIN USING A COMBINATION OF VITAMIN A AND ALPHAHYDROXY ACIDS

(75) Inventor: James E. Fulton, Jr., Newport Beach, CA (US)

(73) Assignee: Vivant Pharmaceuticals, Newport Beach, CA (US)

( * ) Notice: Under 35 U.S.C. 154(b), the term of this patent shall be extended for 0 days.

(21) Appl. No.: 08/861,502

(22) Filed: May 22, 1997

Related U.S. Application Data

(63) Continuation-in-part of application No. 08/755,544, filed on Nov. 21, 1996, now abandoned.
(60) Provisional application No. 60/007,410, filed on Nov. 21, 1995.

(51) Int. Cl.[7] ............... A61K 31/35; A61K 31/185; A61K 31/07; A61K 31/05
(52) U.S. Cl. ............ 514/460; 514/578; 514/725; 514/734; 514/947
(58) Field of Search ............. 514/460, 578, 514/725, 734, 947

(56) References Cited

U.S. PATENT DOCUMENTS

| | | | |
|---|---|---|---|
| 3,729,568 | 4/1973 | Kligman | 424/318 |
| 3,920,835 | 11/1975 | Van Scott et al. | 424/311 |
| 4,572,915 | 2/1986 | Crooks | 514/458 |
| 4,603,146 | 7/1986 | Kligman | 514/559 |
| 5,043,356 | 8/1991 | Fulton, Jr. | 514/549 |
| 5,091,171 | 2/1992 | Yu et al. | 424/642 |
| 5,153,230 | * 10/1992 | Jaffery | 514/847 |
| 5,554,652 | * 9/1996 | Yu et al. | 514/557 |

* cited by examiner

Primary Examiner—Kimberly Jordan
(74) Attorney, Agent, or Firm—Knobbe, Martens, Olson & Bear, LLP

(57) ABSTRACT

Methods of accelerating skin rejuvenation and methods of skin care treatment are disclosed using a combination of vitamin A and alphahydroxy acids, such as the combination of vitamin A propionate and glycolic acid. The combination can be prepared in an alcohol-based carrier having concentrations ranging from approximately 0.01% to 10% vitamin A propionate, preferably 0.1% to 4%, and 0.1% to 30% glycolic acid, preferably 2% to 10% glycolic acid. In addition to alcohol, the carrier may also include propylene glycol, preservatives, thickeners and non-ionic surfactants or may be a cream or ointment-based formulation. The formulation is applied topically to the skin at a frequency which will produce a fine desquamation. The formulation may also be used to accelerate the penetration of other therapeutic agents into the skin.

17 Claims, No Drawings

REJUVENATING THE SKIN USING A COMBINATION OF VITAMIN A AND ALPHAHYDROXY ACIDS

RELATED APPLICATION

This application is a continuation-in-part of U.S. application Ser. No. 08/755,544, filed Nov. 21, 1996, which is abandoned upon the filing of the present application, and which claims priority under 35 U.S.C. § 119(e) from provisional application Ser. No. 60/007,410, filed Nov. 21, 1995.

BACKGROUND OF THE INVENTION

Excessive sun exposure and exposure to the environment causes anatomical degradation of skin which accumulates over time. Every time the skin is photo-damaged or oxidized with therapeutic products such as benzoyl peroxide, the damage produces permanent effects on skin. Although the skin has an ability to repair such damage at an early age, with aging and the depression of the immune system, the ability of the skin to spontaneously repair itself is lost. Alterations in the skin resulting from such damage are apparent microscopically at an early age. As time goes by, the consequences of such degradation accumulate, with the effects being most pronounced at areas of excessive exposure, such as the skin around the eyes. The effects of the damage become visible to the unaided eye as more cells begin to degenerate. In adulthood, these degenerative effects may be seen clinically as blotchy hypo- and hyperpigmentation, keratoses, rhagades, (wrinkles), a general appearance of leathery skin, skin growths and finally, skin cancer. Red-haired and blond, blue-eyed individuals who are raised in the sunbelt are particularly sensitive to such skin damage.

It has been known for centuries that eating fruits and vegetables led to the improved appearance of skin. Early research showed that vitamin A was responsible for the benefits of fruits and vegetables and that it acted by stimulating new cell growth in the epithelium, producing softer, smoother skin. In the late 1930's and the early 1940's, vitamin A was synthesized and became available as a therapeutic agent. From that time forward, it has been recognized that vitamin A is an essential vitamin for the nutrient health of the skin.

In early skin treatments based on reaping the benefits of vitamin A, the vitamin was administered internally in large doses, usually in the form of an ester of vitamin A called vitamin A palmitate. However, internal administration of these esters proved toxic and produced hypervitaminosis A, a cluster of toxic symptoms such as hair loss, migraine headache, fatigue, bone pain and congenital defects.

U.S. Pat. No. 3,729,568 disclosed that repeated topical applications of vitamin A acids to areas of the skin alleviated these symptoms. Although the treatments disclosed in this patent were targeted predominately at the treatment of acne vulgaris, vitamin A became a general topical therapeutic agent well-known to the art of dermatology.

Later, U.S. Pat. No. 4,603,146 disclosed the beneficial effect of this vitamin A acid on retarding the effects of aging on skin. This patent disclosed that vitamin A acid results in a lightening of skin, diminished wrinkling and disappearance of early sun damaged spots such as actinic keratoses. However, treatment with this vitamin A acid causes excessive visible irritation and inflammation of the skin. During the initial months of this treatment, the skin exhibited an abnormal redness or erythema followed by painful, unpleasant peeling of the skin which could be severe. Large chunks of skin are sloughed from the surface, giving the appearance of peeling, or in the case of the scalp, dandruff. This is seen clinically as surface roughness along with abnormal redness. Not only is this cosmetically undesirable, but it is painfully uncomfortable to the patient. This discomfort is particularly amplified when used on skin that has been peeled from the daily use of vitamin A acid. As a consequence of this severe irritation, the use of vitamin A acid as a skin treatment has been limited and must be carefully monitored. Furthermore, the treatment is dispensed only at a physician's prescription request.

Simultaneous to these developments, Dr. Van Scott was developing alphahydroxy acids as skin care products. His initial U.S. Pat. No. 3,920,835 disclosed that the repeated topical application of alphahydroxy acids produced effects similar to those obtained with vitamin A acids. Topical administration of alphahydroxy acids produced an increase in the skin turnover, a general lightening of the skin, and a removal of skin keratoses.

The alphahydroxy acid treatments were not as effective as the vitamin A acid treatments. Using alphahydroxy acids, it was difficult to produce visible peeling and to slough out the acne impactions or to peel off the keratoses. In addition, the high concentrations of alphahydroxy acids required to produce such effects resulted in excessive burning, erosions, or even scarring when applied to the skin.

As a result of the above disclosures, it is known in the dermatologic community that either vitamin A acid or alphahydroxy acids induces skin proliferation and new cell growth. Because of the rapid stimulation of skin proliferation and new cell growth, these individual ingredients are effective in the treatment of acne and other hyperkeratotic skin conditions. Normally, the turnover of skin is 28 days for a new cell to form and then, finally, shed itself off at the surface. Both these compounds reduce this regenerative time to between 10 and 15 days. The regenerative portion of the skin, the epidermis, is doubled in thickness to compensate for this stimulation. However, the top layer of skin, the stratum corneum, is reduced from 14 layers of impacted cells to 8 or 9 layers of loosely woven cells. Deeper down in the skin, in the dermals, there is new collagen formation and new blood vessel formation puffing out the skin and reducing the visible signs of aging.

SUMMARY OF THE INVENTION

The present invention relates to improved methodologies and improved associated pharmaceutical compositions for therapeutically reducing the effects of skin damage and for the treatment of various dermatologic disorders such as acne without the abrasive and irritating characteristics of previous compounds such as vitamin A acid. Preferentially, the compositions of the present invention are applied topically in the form of lotions, including cream vehicles.

The combination of vitamin A and/or natural or synthetic derivatives of vitamin A, such as beta-carotene and retinoic acid, and alphahydroxy acids and/or hetahydroxy acid is effective for rejuvenation of human skin, treatment of skin disorders, and the general improvement of the quality and appearance of skin. Additionally, the combination provides an effective method to retard and reduce the effects of photoaging and environmental damage on skin. Particularly, the combination is effective in treating hyperkeratotic skin diseases such as acne vulgaris, disorders of keratinization such as ichthyosis, Darier's disease, acne, psoriasis and other similar conditions, early skin degenerations and precancerous conditions such as actinic keratoses, lentigos, lentigo malignas and melasma.

Preferably, the vitamin A or natural or synthetic derivative of vitamin A, such as betacarotene and retinoic acid, is covalently linked to an acid or an aldehyde through an esterbond.

Acids which can be ester linked to the vitamin A, or natural or synthetic derivative thereof, can comprise from 2–25 carbons, and can be linear, cyclic, or branched, and can be substituted or unsubstituted. Preferably the acid comprises 2–16 carbons. In especially preferred embodiments, the acid which is ester linked to the vitamin A or natural or synthetic derivative thereof is acetate, propionate, or palmitate.

Preferred aldehydes which are suitable for covalent linkage to the vitamin A, or natural or synthetic derivative thereof, can comprise from 2–25 carbons, can be linear, cyclic, or branched, and can be substituted or unsubstituted. Preferably the aldehyde comprises 2–16 carbons.

The alphahydroxy acids used in the present formulations can comprise from 2–25 carbons, may be linear, cyclic, or branched, and may be substituted or unsubstituted. Preferably, the alphahydroxy acid comprises 2–10 carbons. More preferably, the alphahydroxy acid is citric acid, lactic acid, or glycolic acid.

Betahydroxy acids can also be included in the vitamin A formulation. The betahydroxy acids may comprise 2–25 carbons, may be linear, cyclic, or branched, and may be substituted or unsubstituted. Preferably, the betahydroxy acid comprises 2–10 carbons. A preferred betahydroxy acid is salicylic acid. A preferred vitamin A/alphahydroxy acid combination is vitamin A propionate/glycolic acid. The viatmin A propionate may be present at a concentration of about 0.1% to 10%. Preferably, the vitamin A propionate is present at a concentration of about 0.1% to 4%. Preferably, the glycolic acid is present at a concentration of about 2% to 10%. This formulation is distinct from previous compositions which employed long chain esters such as vitamin A palmitate alone. Vitamin A palmitate alone is ill suited for use in externally applied lotions because it is too large a molecule to effectively penetrate into the skin.

Additionally, the present combination is distinct from prior formulations which employed vitamin A propionate alone. This formulation is also distinct from previous compositions employing alphahydroxy acids such as glycolic acid, lactic acid and citric acid by themselves. The combination of vitamin A with alphahydroxy acids is more effective than alphahydroxy acids alone.

The compositions and methods of the present invention provide advantages over the currently used treatments of the above conditions. For example, because the combination of vitamin A with alphahydroxy acids causes cells to fall off one at a time, the large chunks of peeling caused by treatment with vitamin A acid alone is avoided. Thus, the present invention achieves the benefits of increased turnover of skin without the detrimental visible effects of prior treatments. Additionally, with the present invention the treatments are easier for patients to tolerate and to disguise by applying make-up.

The present invention also provides advantages over current treatments of acne vulgaris. Using the present invention, the unpleasant side effects associated with oxidizing the skin with benzoyl peroxide and the skin irritation caused by detergents are avoided.

In addition to its application as a direct treatment of skin disorders, the present invention is also uniquely effective in increasing the penetration of other active molecules. Examples of such other active molecules include antiftmgals such as Ketoconazole or Tolnafate, anti-cancer agents such as Methotrexate or 5-Fluorouracil, and anti-bacterial agents such as Chlorhexidine or Gentamicin. The active agents can also comprise a bleaching agent. Preferably, the bleaching agent is a mild oxidizing agent suitable for application to the skin, including quinone-like compounds such as hydroquinone or kojic acid. Unexpectedly, as evidenced below in Example 7, when bleaching agents are incorporated into the compositions of the present invention, a several fold increase in bleaching effectiveness is obtained. Such additional agents can be combined with the compositions of the present invention by incorporating them in the carrier base of lotions containing a combination of vitamin A and alphahydroxy acids.

Another objective of the present invention is to develop a method of maintaining the skin in its rejuvenated state over a long period of time, thereby avoiding the visible effects of skin damage or aging. The present compositions and skin care regimens provide a refreshing renewal of the skin on a long-term basis.

Further features and advantages of the present invention shall become apparent to those skilled in the art from the consideration of the following detailed description of the invention.

DETAILED DESCRIPTION OF THE PREFERRED EMBODIMENT

Generally stated, this invention is based upon the discovery that appropriately formulated and allied combinations of vitamin A and alphahydroxy acid compositions unexpectedly exhibit a high degree of skin regenerative activity without the associated peeling, erythema and irritant effects of the use of vitamin A acid alone. The present invention is useful in reducing the visible effects of skin damage or aging. The present invention also finds application in treating numerous skin disorders and conditions, as well as benign epidermal tumors. The present invention may also be used to enhance the penetration of other active substances into the skin. Furthermore, the present invention produces these benefits without the excessive peeling associated with vitamin A acid treatment or the burning associated with glycolic acid treatment. The therapeutic properties of the combination of the present invention are especially surprising in light of the absence of similar properties of other derivatives such as the alcohol and ester forms of vitamin A.

For purposes of illustration only and without limiting the scope of the present invention, the following description includes combination systems for delivering vitamin A propionate and glycolic acid topically to the area of skin. However, it is understood that those skilled in the art in the use of vitamin A and the use of alphahydroxy acids may be aware of a large variety of applications used for treating skin disorders and conditions responsive to induced proliferation and increased epidermal penetration. In order to fully describe the invention and its superior properties for the treatment of skin disorders, the following examples are offered. It is understood that these examples do not limit the scope of the invention.

Preferably, the compositions produced in accordance with the teachings of the present invention will be gels that are easily applied to the skin. Alcohol based or cream based carriers can be used to deliver therapeutic amounts of the present combinations of active agents to the skin. The alcohol gels are preferred for applications on the face where a high-potency effect is required. Although not essential to the practice of the present invention, the handling characteristics of the alcohol-based carrier system in the present invention can be varied by addition of thickening agents which add body to the composition and are capable of increasing the viscosity of the alcohol base. Hydroxypropyl celluloses are particularly effective as thickening agents. The amount of the thickening agent depends upon the desired consistency and viscosity. Those skilled in the art will appreciate that the carrier system contain the thickening agents with viscosity characteristics can be dependent upon the non-polarity or polarity of the solvent system, the pH, and that other thickeners may be added to meet these requirements.

The combination of vitamin A and alphahydroxy acids can also be applied to the skin in a cream vehicle. Overall, the cream ointment vehicles are not as effective as the alcohol gels. The more subtle effects of a cream base over a longer period of time may be beneficial, on the arms and legs for ichthyosis and actinic keratoses. The cream vehicles should be a special formulation that allow the active ingredients to diffuse into the skin and are not irritating or comedogenic such that they may be used without causing dermatitis or the flaring up of acne conditions.

Other non-irritating additives may be useful to prolong the shelf life, such as preservatives or to beneficially aid the user, such as sunscreens. There are appropriate components for the present invention that have additional benefits of protecting the skin and adding as natural moisturizers to prevent further skin dehydration and sun damage. Among such additives are sunscreens such as para-aminobenzoic acid and its derivatives, extract of aloe vera plants and often common lotion additives such as sodium, PCA, sodium lactate, urea, nicotinamide, fructose and other natural conditions and moisturizers of skin.

It is also contemplated as being within the scope of this present invention to increase the shelf life of the compositions by adding preservatives in the amounts that do not alter the safety and efficacy of the preparation, but preserve its usefulness. Any compatible preservative which is pharmaceutically active is appropriate for this application. Preferred preservatives are butylated hydroxy toluene and methyl and propylparaben and phenoxyethenol.

It is also contemplated as being within the scope of this present invention to add other therapeutically active additives that are commonly in externally applied lotions. The combination of additional active ingredients are more effective when applied in these vehicles. Other active molecules may become more potent in the presence of these formulations that increase the metabolism of the skin. These will include sun protectives such as sun screen, anti-fimgals such as Ketoconazole, anti-bacterials such as Chlorhexidine, and anti-cancer agents such as 5-Fluorouracil. As discussed above, the agent can also comprise a bleaching agent.

An exemplary vitamin A, alphahydroxy acid composition is prepared as follows.

Example 1

Preparation of an Alcohol Based Composition Useful in the Treatment of Skin Disorders a. Add 2.2 grams of vitamin A propionate to 70 grams of alcohol (SD40-A) and mix. (Formulation A)

b. Add 5 grams of glycolic acid to 20 grams of propylene glycol and mix. (Formulation B)

c. Blend Formaulation A and Formulation B at room temperature until the solution is homogeneous.

d. Sift in 4 grams of hydroxypropyl cellulose slowly over approximately 15 minutes while blending to avoid clumping.

e. While stirring, add 5.0 grams of extract of the aloe vera plant and 0.1 grams of Lactil.

f. Stir gently until cellulose is dissolved.

Example 2 demonstrates that the compositions of the present invention produce a dramatic increase in the size of the epidermal cell population. Furthermore, synergistic effects were observed when a combination of vitamin A propionate and glycolic acid was administered.

Example 2

Guinea Pig Epidermal Proliferation Study

The vitamin A propionate-glycolic acid formulation described in Example 1 was applied to the back of six hairless guinea pigs. This controlled study included (1) the formulation without vitamin A and glycolic acid (2) the formulation with the glycolic acid at 5% and (3) the formulation with the vitamin A propionate at 2% and (4) a control of vitamin A acid 0.01%. The applications were continued for 14 days, after which biopsies were taken from the treated sites. After fixation in formaldehyde and sectioning in paraffin, the sections were stained with hematoxlin eosin. The number of epidermal cells within a 100 micron area was counted at these five treated sites. Table 1 lists the results. The synergy of the vitamin A propionate/glycolic mixture was apparent. There was a dramatic increase in the size of the epidermal cell population.

TABLE 1

| EPIDERMAL PROLIFERATION STUDY | |
|---|---|
| FORMULATION | INCREASE IN NEW CELLS |
| Vitamin A Propionate/Glycolic | 27.2% |
| Vitamin A Acid .01% | 22.1% |
| Vitamin A Propionate | 12.5% |
| Glycolic | 10.2% |
| Vehicle | 5.0% |

Example 3 demonstrates that the present compositions were effective in reducing the depth of crow's feet.

Example 3

Computer Imaging for Contour Analysis

Twelve human subjects applied the vitamin A propionate glycoic lotion to the right lateral eyelid area in the area of crow's feet. The vehicle was used in a similar area in the left lateral eyelid area of crow's feet. The two formulations were applied daily for one month. A contour analysis which provides quantified values and three-dimensional graphic representations of the skin surface was performed on all subjects before and after one month of treatment. The skin smoothness and wrinkle depth was recorded and compared to their pre-treatment value. There was a 21.2% improvement in the depth of superficial fine lines on the active formulation side and a 3.5% improve ment in the depth of fine lines on the vehicle t reated side.

Example 4 demonstrates that the present compositions were effective in reducing the thickness of the stratum corneum.

Example 4

Transepidermnal Water Loss

The use of the rate of transepidermal water loss (TEWL) is a well recognized means for measuring the stratum corneus thickness. The TEWL increases when the top layer of stratum corneums are reduced in thickness. Twelve subjects were treated on the forehead with the combination formula on the right side and the vehicle on the a left. The TEWL was measured before and after the treatment using the method of Baker and Kligman (Journal of Investigative Dermatology 86:441–452, 1967), the disclosure of which is hereby incorporated by reference. There was a 28% increase in transepidermal water loss at the combination treated site relative to the control site.

The compositions of the present invention are effective in increasing the penetration of other active agents into the skin, as shown in the experiments of Example 5.

Example 5

The Dansyl Chloride Penetration Study

Dansyl Chloride is the fluorescent molecule that penetrates through the skin. The rate of penetration is dependent upon the number of layers of the intact stratum corneum. The reduced stratum corneum would allow for more rapid penetration of Dansyl Chloride and other similar types of molecules. The inner aspect of the right forearm was treated on ten subjects with the combination vitamin A propionate/glycolic acid conditioning lotion. The other forearm was treated with the vehicle alone. After two weeks of twice daily applications, the Dansyl Chloride penetration test was conducted. The 10% Dansyl Chloride in petroleum was applied on a 1 cm patch to six separate areas. Every 15 minutes, one patch was swabbed with alcohol, and after drying, the area was stripped with Scotch tape to measure the penetration of the molecules through the stratum corneum. As each pull of the scotch tape removed one layer of stratum corneum, this is an index of penetration. Once the Dansyl Chloride has penetrated to the viable epidermis, it can be no longer stripped off. Every 15 minutes a new site was re-examined. The penetration through the combination treated site occurred in 30 minutes. The penetration through the vehicle-controlled site took 75 minutes. This increased penetration shows the efficacy of the active formulation in conditioning the skin to permit the penetration of other molecules on a more rapid basis.

Example 6 describes the results of experiments demonstrating the efficacy of the present compositions as a treatment for acne vulgaris. With the present compositions, a 60% reduction in the effects of acne vulgaris was obtained.

Example 6

Clinical Observations of the Vitamin A Propionate/ Glycolic Users in the Treatment of Acne Vulgaris 215 human subjects with acne complexions were treated twice daily with the combination vitamin A propionate/glycolic acid formulation. Those treated for impacted pores for their acne condition, there was significant evacuation of the build-up of debris and subsequent complexion clearing. The number of acne lesions was divided into five categories: open comedones, closed comedones, papules, pustules and cysts. These lesions on the left side of the face were counted every two weeks during the two-month study. Sixty percent reduction in acne lesions is documented.

TABLE II

Reduction in Acne Lesions During Vitamin A Propionate/Glycolic Acid

| | Before | After | Treatment % Reduction |
| --- | --- | --- | --- |
| Open Comedones | 15 | 8 | 47 |
| Closed Comedones | 35 | 10 | 71 |
| Papules | 12 | 7 | 42 |
| Pustules | 8 | 4 | 50 |
| Cysts | 3 | 1 | 67 |
| TOTAL | 73 | 29 | 60 |

Example 7

Fifteen human subjects with blotchy pigmentation of the face (melasma) were treated twice daily with a combination of the bleaching agent hydroquinone (present at a concentration of 2%) in the vitamin A propionate/glycolic acid gel on one side of the face and hydroquinone (present at a concentration of $^2$%) in a conventional cream base (Eldoquin®) on the other side of the face. Every two weeks, the percent reduction in pigment was monitored with optical reflectometry using a Bausch and Lomb Model 41 5-A reflectometer. After eight weeks there was a $^{37}$% reduction in pigment on the gel treated side and an 8% reduction in pigment on the cream treated side.

Without further elaboration, it is believed that one skilled in the art can, using the preceding description, utilize the invention to its fuillest extent. The invention may be embodied in other specific forms without departing from its spirit of essential characteristics. The described embodiments are to be considered in all respects only as illustrative and not restrictive, and the scope of the invention is therefore indicated by the appended claims rather than by the foregoing description. All modifications which come within the meaning and range of the lawful equivalency of the claims are to be embraced within their scope.

What is claimed is:

1. A composition for the treatment of skin disorders or for rejuvenation of the skin comprising a therapeutic amount of vitamin A propionate and glycolic acid in a pharmaceutically acceptable carrier.

2. The composition of claim 1 wherein the vitamin A propionate is present at a concentration of about 0.01% to 10%.

3. The composition of claim 2 wherein the vitamin propionate is present at a concentration of about 0.1 % to 4%.

4. The composition of claim 3 wherein said glycolic acid is present at a concentration of about 0.1% to 30%.

5. The composition of claim 4 wherein said glycolic acid is present at a concentration of about 2% to 10%.

6. The composition of claim 1 wherein the carrier is a cream.

7. The composition of claim 1 wherein the carrier is an alcohol gel.

8. The composition of claim 7 wherein the alcohol in said alcohol gel is SD40-A.

9. The composition of claim 1 further comprising a thickening agent.

10. The composition of claim 9 wherein said thickening agent is hydroxypropyl cellulose.

11. The composition of claim 1 further comprising a therapeutic amount of an additional active agent.

12. The composition of claim 11 wherein said active agent is selected from the group consisting of sunscreens, antifungal agents, antibacterial agents, and anticancer agents.

13. The composition of claim 11 further comprising a preservative.

14. A method of enhancing the penetration of an active agent through the skin comprising administering a composition comprising a therapeutic amount of vitamin A prooionate and glycolic acid and a therapeutic amount of an active agent in a pharmaceutically acceptable carrier to the skin to the skin.

15. The method of claim 14, wherein said active agent comprises a bleaching agent.

16. The method of claim 15, wherein said bleaching agent comprises a quinone-like compound which is a mild oxidizing agent suitable for application to the skin.

17. The method of claim 15, wherein said bleaching agent is selected from the group consisting of hydroquinone and kojic acid.

* * * * *